(12) United States Patent
Tang et al.

(10) Patent No.: US 11,940,366 B1
(45) Date of Patent: Mar. 26, 2024

(54) CENTRIFUGAL TESTING DEVICE AND METHOD FOR SIMULATING GROUND SUBSIDENCE INDUCED BY BURIED PIPELINE LEAKAGE AND INFILTRATION

(71) Applicant: ZHEJIANG UNIVERSITY, Hangzhou (CN)

(72) Inventors: Yao Tang, Hangzhou (CN); Qingguo Yang, Hangzhou (CN); Bo Huang, Hangzhou (CN); Yunmin Chen, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 18/388,535

(22) Filed: Nov. 10, 2023

Related U.S. Application Data

(63) Continuation of application No. PCT/CN2023/086065, filed on Apr. 4, 2023.

(30) Foreign Application Priority Data

Jun. 14, 2022 (CN) .......................... 202210670677.0

(51) Int. Cl.
 *G01N 15/08* (2006.01)
 *G01N 3/12* (2006.01)
 *G01N 33/24* (2006.01)

(52) U.S. Cl.
 CPC .......... *G01N 15/0806* (2013.01); *G01N 3/12* (2013.01); *G01N 33/246* (2013.01); *G01N 2203/0075* (2013.01)

(58) Field of Classification Search
 CPC .... G01N 15/0806; G01N 3/12; G01N 33/246; G01N 2203/0075

(Continued)

(56) References Cited

U.S. PATENT DOCUMENTS

2022/0179122 A1* 6/2022 Tan .................. G01V 20/00

FOREIGN PATENT DOCUMENTS

| CN | 1749624 A | * | 3/2006 |
| CN | 106018736 A | * | 10/2016 |

(Continued)

OTHER PUBLICATIONS

Chen Yun-Min, et al., Development of geotechnical centrifuge ZJU400 and performance assessment of its shaking table system, Chinese Journal of Geotechnical Engineering, 2011, pp. 1887-1894, vol. 33, No. 12.

*Primary Examiner* — Marrit Eyassu
(74) *Attorney, Agent, or Firm* — Bayramoglu Law Offices LLC

(57) ABSTRACT

A centrifugal testing device for simulating ground subsidence induced by buried pipeline leakage and infiltration includes a model box provided with a transparent observation window at a front side, a chamber partitioning plate, a damaged pipeline model, permeable plates, and a water-soil separation device. A front part of the model box is divided into a test soil chamber for filling model soil and seepage chambers located at two sides of the test soil chamber. A rear part of the model box is divided into a soil filtration chamber and water circulation supply chambers located at two sides of the soil filtration chamber. The damaged pipeline model includes a front end provided with an electric push rod for controlling a crack of the damaged pipeline model to be opened and closed and a rear end provided with a ball valve device and connected to a water pump.

13 Claims, 9 Drawing Sheets

(58) Field of Classification Search
USPC .............................................................. 73/38
See application file for complete search history.

(56) References Cited

FOREIGN PATENT DOCUMENTS

| | | | | |
|---|---|---|---|---|
| CN | 106018736 A | | 10/2016 | |
| CN | 107505448 A | * | 12/2017 | ............. G01N 33/24 |
| CN | 107505448 A | | 12/2017 | |
| CN | 108037267 A | | 5/2018 | |
| CN | 208255017 U | | 12/2018 | |
| CN | 109147541 A | * | 1/2019 | ............. G01N 33/24 |
| CN | 110044795 A | | 7/2019 | |
| CN | 110333334 A | | 10/2019 | |
| CN | 110543680 A | | 12/2019 | |
| CN | 210109107 U | | 2/2020 | |
| CN | 112578101 A | | 3/2021 | |
| CN | 113049773 A | | 6/2021 | |
| CN | 115165242 A | | 10/2022 | |
| KR | 20170119255 A | | 10/2017 | |

* cited by examiner

CENTRIFUGAL TESTING DEVICE AND METHOD FOR SIMULATING GROUND SUBSIDENCE INDUCED BY BURIED PIPELINE LEAKAGE AND INFILTRATION

CROSS REFERENCE TO THE RELATED APPLICATIONS

This application is the continuation application of International Application No. PCT/CN2023/086065, filed on Apr. 4, 2023, which is based upon and claims priority to Chinese Patent Application No. 202210670677.0, filed on Jun. 14, 2022, the entire contents of which are incorporated herein by reference.

TECHNICAL FIELD

The present disclosure belongs to the field of civil engineering, and in particular to a centrifugal testing device and method for simulating ground subsidence induced by buried pipeline leakage and infiltration.

BACKGROUND

With the continuous increase of China's urbanization rate, buried pipelines such as rainwater and sewage pipelines and communication pipelines have become important infrastructure to ensure urban functions. Due to factors such as extended service, manufacturing defects and construction disturbances, the walls and joints of buried pipelines are prone to damage. In areas with excellent hydraulic conditions, such as areas with high groundwater levels and areas with high rainfall during the rainy season, due to the infiltration of water into the damaged pipeline, the foundation soil is lost through the damaged pipeline. Besides, in the case of large precipitation, there is a full flow inside the damaged pipeline, which will lead to water leakage that exacerbates soil degradation. Due to water leakage and infiltration, seepage erosion in the foundation soil continues to develop, and the mechanical properties of the soil deteriorate. Under external loads, it will cause serious consequences such as foundation instability and subsidence. These types of disasters feature concealment and suddenness, and are more common in urban areas, especially in densely populated areas and industrial areas with developed underground pipelines. Once such disasters occur, they will cause significant loss of life and property, and cause negative social impact. Ground subsidence disasters caused by damaged buried pipelines feature strong concealment and serious consequences. In addition, pipelines that have been in service for a long time have a large damage rate and a large disaster risk. The process of ground subsidence caused by damaged buried pipelines is significantly different from the traditional mechanism of foundation instability, and is closely related to soil seepage erosion. However, there is currently insufficient research on this damage mechanism, and there is a lack of effective prevention and control measures.

In the field of scientific research, physical simulation tests are an important means to discover the objective properties of things and reveal the laws of their development. Hypergravity technology can be used to achieve the purposes of scale reduction, time reduction, and restoring the true stress state. Therefore, a centrifuge can be used to provide hypergravity to study the related issues of ground subsidence caused by buried pipeline leakage and infiltration, so as to reveal the evolution laws of pore pressure and ground deformation during the process of ground subsidence. There are currently no reports on a centrifugal model testing device for simulating ground subsidence induced by buried pipeline leakage and infiltration through a hypergravity method.

SUMMARY

The present disclosure proposes a hypergravity centrifugal model testing device and method for reproducing a triggering and evolution process of ground subsidence caused by buried pipeline leakage and infiltration under the action of a true stress level.

To achieve the above objective, the present disclosure adopts the following technical solutions.

The present disclosure provides a centrifugal testing device for simulating ground subsidence induced by buried pipeline leakage and infiltration. The centrifugal testing device includes a model box, a damaged pipeline model, a servo control system, and a monitoring and sensing system, where the model box is internally divided into a front part and a rear part by a chamber partitioning plate; and the chamber partitioning plate is provided with a mounting hole for fixing the damaged pipeline model;

the front part of the model box is provided with a test soil chamber and seepage chambers located at two sides of the test soil chamber; a front end of the damaged pipeline model in the test soil chamber is provided with a crack having an adjustable size; the rear part of the model box is provided with a soil filtration chamber and water circulation supply chambers located at two sides of the soil filtration chamber; a rear end of the damaged pipeline model in the soil filtration chamber is provided with a water inlet and outlet control device; a water-soil separation device is provided below the water inlet and outlet control device; and the chamber partitioning plate is provided with a water level limiting hole for communicating the seepage chamber with the water circulation supply chamber; and the servo control system is configured to resize the crack of the damaged pipeline model and control water levels inside and outside the damaged pipeline model; and the monitoring and sensing system is configured to measure a soil pressure, a water pressure and a soil surface displacement of the test soil chamber and a strain of the water-soil separation device in the soil filtration chamber in real time.

Further, the damaged pipeline model includes a pipeline body, a front end cover, a rear end cover, and an electric push rod assembly; the pipeline body is fixed into the mounting hole of the chamber partitioning plate through a flange plate; the front end cover and the rear end cover are configured to seal front and rear ends of the pipeline body, respectively; the crack is located at a position of the pipeline body adjacent to the front end cover; the electric push rod assembly is provided at an inner side of the front end cover; and a rubber plug at an end of an electric push rod is configured to resize the crack.

Further, the water inlet and outlet control device is provided with a ball valve device; and the ball valve device is provided on the rear end cover to switch the damaged pipeline model between water inlet and outlet conditions.

Further, the soil filtration chamber is separated from the water circulation supply chambers at the two sides of the soil filtration chamber by a pair of baffles; a bottom part of the baffle is provided with a hole for communicating the soil filtration chamber with the water circulation supply chamber; and the water-soil separation device is fixed inside the soil filtration chamber by the baffles and located below the damaged pipeline model.

Further, the water-soil separation device is a single-layer or multi-layer filter plate.

Further, a submersible pump is provided in the water circulation supply chamber; and the submersible pump is connected to the water inlet and outlet control device of the damaged pipeline model and the seepage chamber through a controllable water outlet pipe.

Further, the monitoring and sensing system includes a strain monitoring assembly, pore pressure sensors, soil pressure sensors, a laser displacement sensing device, and a high-speed camera assembly; and the pore pressure sensors and the soil pressure sensors are arranged in a line array in different layers in soil inside the test soil chamber; the laser displacement sensing device is provided in a line array above the test soil chamber to measure a soil surface displacement inside the test soil chamber; the strain monitoring assembly is provided on the water-soil separation device to measure the strain of the water-soil separation device; and the high-speed camera assembly is provided at an observation window at a front plate of the model box.

Further, the servo control system includes a servo controller and a plurality of servo actuators; and each of the servo actuators is configured to adjust a circulating water volume and a flow direction of the water circulation supply chambers, switch the water inlet and outlet control device between water inlet and outlet functions, and resize the crack of the damaged pipeline model.

The present disclosure has following beneficial effects:

1. The present disclosure combines a water pump and servo control system composed of the submersible pumps, a water pressure gauge, and the servo control system with the water circulation supply chambers, the permeable plates, and the ball valve device to achieve water circulation of the testing device, and can adjust the water levels inside and outside the pipeline in real time.

2. The present disclosure innovatively proposes a hypergravity-based leakage and infiltration simulation technology, and reflects the true stress state and hydraulic conditions of damaged buried pipelines in different seasons and regions through hypergravity tests, achieving the leakage and infiltration simulation technology through the geotechnical centrifugal buried pipeline model.

3. The present disclosure creatively proposes a real-time monitoring technology for soil particle escape under hypergravity. The present disclosure designs the soil filtration chamber for sorting the water-soil mixture based on a mechanical principle, and designs a strain detection assembly on the filter plate to accurately derive a real-time detection curve reflecting the escape of soil particles.

4. The present disclosure combines a high-speed camera and a transparent window to capture the testing process, and quantitatively analyzes the soil state under a pipeline damage condition through particle image velocimetry (PIV) to accurately reflect the deformation trend of the soil in the test soil chamber.

5. The present disclosure dynamically measures the evolution of the pore pressure inside the foundation soil by embedding pore pressure sensors to assist in correcting the work of the water circulation system. The present disclosure monitors the surface deformation of the foundation soil through the laser displacement sensors, and can derive the soil pore pressure and displacement relationship through joint analysis of the data of the pore pressure sensors and laser displacement sensors.

6. The present disclosure can flexibly simulate the crack of the damaged pipeline, and adjust the size and direction of the crack by changing the connection angle between the pipeline and the chamber partitioning plate, achieving a wide range of testing. All water circulation and soil particle migration processes occur inside the model box, without mass communication with the outside world, avoiding significant changes in physical parameters such as mass and centroid, and having little impact on the working state of the geotechnical centrifuge. Therefore, the present disclosure has advantages in stability and accuracy.

In summary, the present disclosure is based on a hypergravity model test, and provides hypergravity through a centrifugal device to restore the internal erosion and instability process of the foundation soil under true stress state and changing hydraulic conditions. The present disclosure provides an analytical method and testing support for revealing the trends of soil deformation and pore pressure changes during foundation subsidence induced by a damaged pipeline.

BRIEF DESCRIPTION OF THE DRAWINGS

To describe the technical solutions in the implementations of the present disclosure more clearly, the drawings required for describing the examples are briefly described below. It should be understood that the following drawings show merely some embodiments of the present disclosure, and thus should not be regarded as a limitation to the scope. A person of ordinary skill in the art may still derive other related drawings from these drawings without creative efforts.

Figure 1:
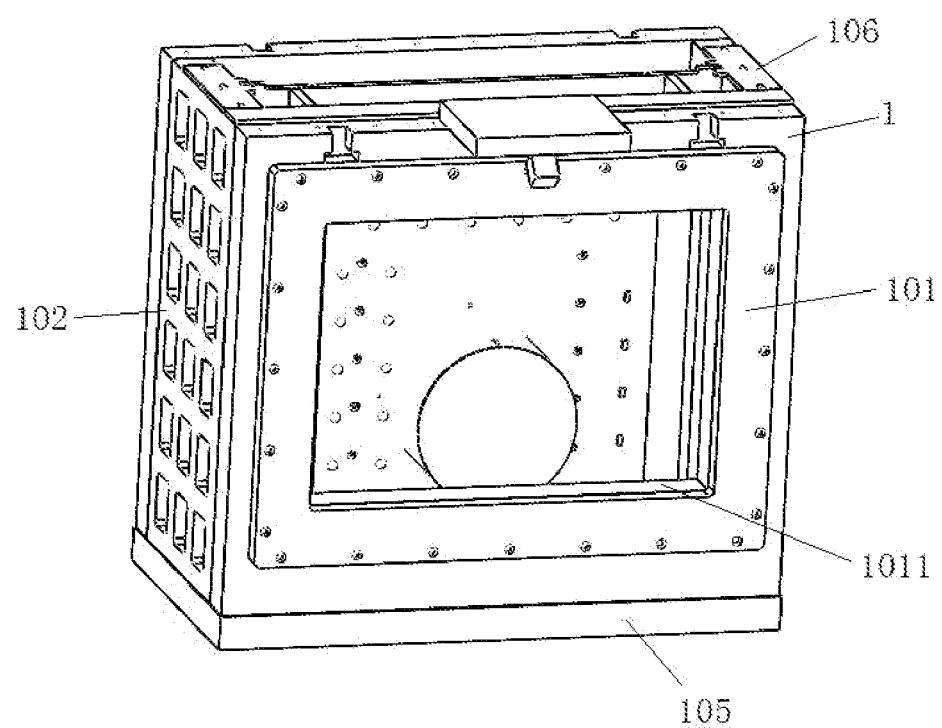
FIG. 1 is an overall structural diagram of a testing device according to an embodiment of the present disclosure.

Reference Numerals: 1. model box; 101. front plate; 1011. observation window; 102. left plate; 103. right plate; 104. back plate; 105. bottom plate; 106. fixing clamp plate; 2. damaged pipeline model; 201. pipeline body; 202. crack; 203. front end cover; 204. rear end cover; 205. ball valve device; 206. electric push rod assembly; 207. rubber plug; 208. flange plate; 301. strain monitoring assembly; 302. pore pressure sensor; 303. soil pressure sensor; 304. laser displacement sensing device; 3041. laser displacement sensor connecting rod; 3042. laser displacement sensor; 305. high-speed camera assembly; 4. chamber partitioning plate; 401. water level limiting hole; 5. permeable plate; 6. baffle; 7.

filter plate; 8. test soil chamber; 9. seepage chamber; 10. soil filtration chamber; 11. water circulation supply chamber; and 12. submersible pump.

DETAILED DESCRIPTION OF THE EMBODIMENTS

In order to make the objectives, technical solutions, and advantages of the implementations of the present disclosure clearer, the technical solutions in the implementations of the present disclosure will be clearly and completely described below in conjunction with the drawings in the implementations of the present disclosure. Obviously, the described implementations are some, rather than all of the implementations of the present disclosure. On the basis of the implementations of the present disclosure, all other implementations obtained by a person of ordinary skill in the art without making creative efforts shall fall within the protection scope of the present disclosure.

Hypergravity technology can achieve the goals of scale reduction, time reduction, and restoring the true stress state. The present disclosure utilizes a centrifuge that provides hypergravity to study the related issues of ground subsidence caused by buried pipeline leakage and infiltration, so as to reveal the evolution law of pore pressure and ground deformation during the process of ground subsidence. There are currently no reports on a centrifugal model testing device for simulating ground subsidence induced by buried pipeline leakage and infiltration through a hypergravity method. Embodiments of the present disclosure can effectively achieve the above purpose, and are described in detail below according to the drawings.

Figure 2:
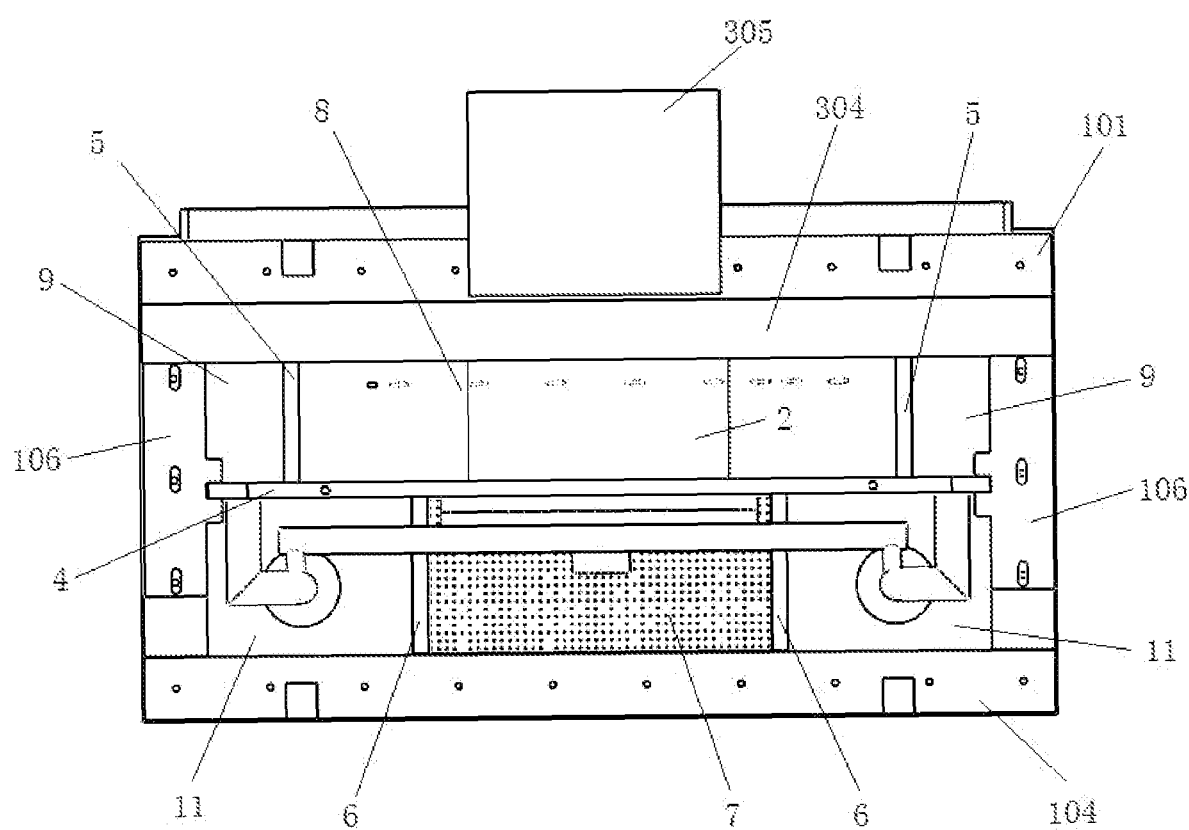
FIG. 2 is a top view of the testing device according to the embodiment of the present disclosure.

As shown in FIGS. 1 and 2, an embodiment provides a centrifugal testing device for simulating ground subsidence induced by buried pipeline leakage and infiltration. The device includes model box 1, damaged pipeline model 2, a servo control system, and a monitoring and sensing system. The model box is internally divided into a front part and a rear part by chamber partitioning plate 4. The chamber partitioning plate 4 is provided with a mounting hole for fixing the damaged pipeline model.

In this embodiment, the model box 1 includes front plate 101 with observation window 1011, back plate 104, right plate 103, left plate 102, and bottom plate 105. These five parts of the model box are all made of steel structures to ensure that the deformation and strength of the model box adapt to the requirements of gravitational acceleration (Ng) and bearing of the test model. The model box can be provided on a centrifuge basket. In addition, the model box 1 is provided with fixing clamp plate 106 for fixing the model box and an internal structure. High-speed camera assembly 305 is provided outside the observation window 1011 for real-time recording of a testing process. The high-speed camera assembly 305 includes a fill light strip, a high-speed camera, and a mounting kit.

The internal structure of the model box includes the chamber partitioning plate 4, a pair of permeable plates 5, and a pair of baffles 6. Each plate is connected by a bolt for easy testing and adjustment. The chamber partitioning plate 4 separates an internal space of the model box into the front part and the rear part. The chamber partitioning plate 4 is provided with a mounting hole for fixing the damaged pipeline model. The front part of the model box is divided by the pair of permeable plates 5 into test soil chamber 8 and seepage chambers 9 located at two sides of the test soil chamber 8. The permeable plates eliminate the scouring effect of water flow on the soil, and reduce the boundary effect of water flow from the seepage chambers to the test soil chamber, so as to effectively reflect the true groundwater infiltration state. The rear part of the model box is divided by the pair of baffles 6 into soil filtration chamber 10 and water circulation supply chambers 11 located at two sides of the soil filtration chamber 10. A bottom part of the baffle is provided with a hole for communicating the soil filtration chamber 10 with the water circulation supply chamber 11. The chamber partitioning plate 4 is provided with water level limiting hole 401 for communicating the seepage chamber 9 with the water circulation supply chamber 11.

Figure 3:
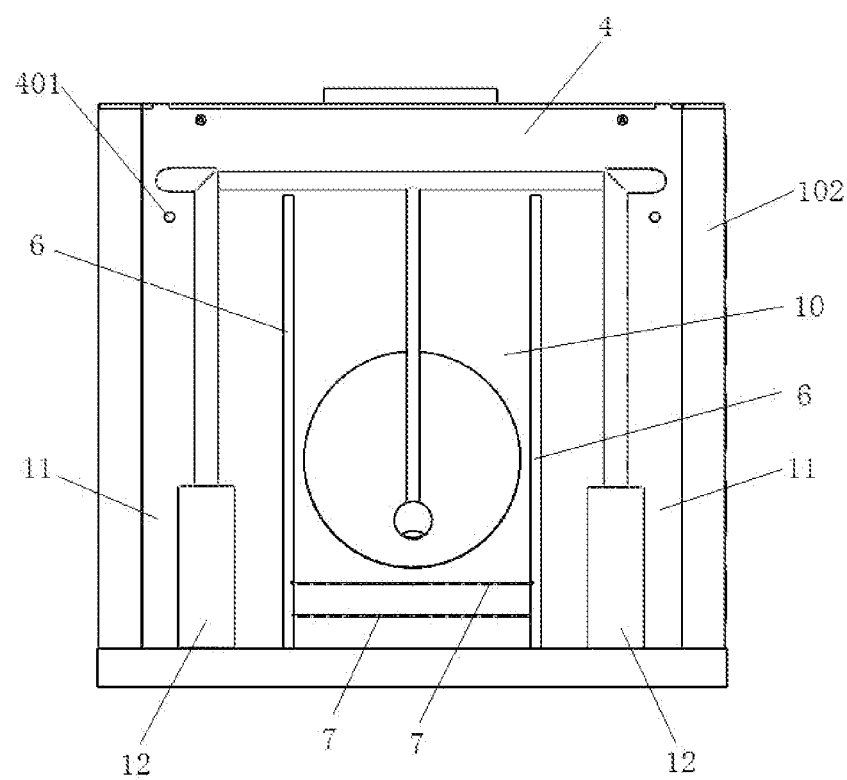
FIG. 3 is a rear view of the testing device (with a back plate of a model box removed) according to the embodiment of the present disclosure.

As shown in FIG. 3, submersible pump 12 is provided in each of the water circulation supply chambers at the two sides. The submersible pump 12 is connected to a water inlet and outlet control device of the damaged pipeline model and the seepage chamber 9 through a controllable water outlet pipe. A water level of the seepage chamber is adjusted by adjusting a height of the water level limiting hole 401, achieving the purpose of controlling a water level outside the damaged pipeline model. The height adjustment of the water level limiting hole can be implemented through prior art. For example, water level limiting holes that can be opened or closed at different heights can be provided. The water inlet and outlet control device can be implemented through ball valve device 205. The ball valve device is provided on rear end cover 204 of the pipeline to switch between water inlet and outlet models of the damaged pipeline model 2.

A water-soil separation device is provided in the soil filtration chamber for graded filtration of a water-soil mixture flowing out of the simulated damaged pipeline. The purpose of the water-soil separation device is to separate water and soil. Soil particles are blocked by a filter plate group, and the water flow freely passes through. In this way, the soil particles are graded and collected by the filter plate group, and the filtered water meets the requirement of the water inlet quality of the submersible pump, facilitating the analysis of soil particle escape behavior. The water-soil separation device can be fixed through preset sockets of the baffles at the two sides.

Figure 4A:
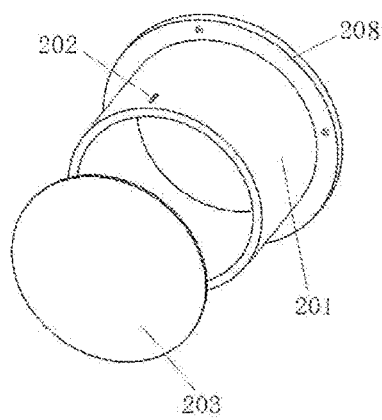
FIGS. 4A-4C are schematic diagrams of a damaged pipeline model.
Figure 4B:
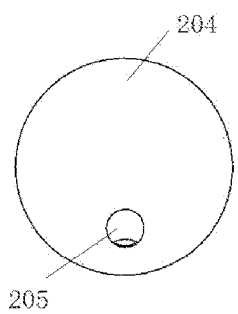
Figure 4C:
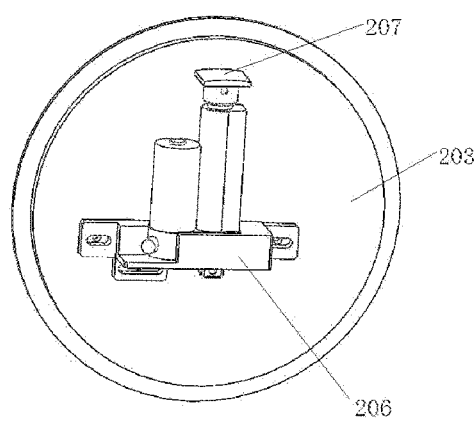

As shown in FIGS. 4A-4C, the damaged pipeline model includes pipeline body 201, front end cover 203, rear end cover 204, and electric push rod assembly 206. The pipeline body 201 is connected to the chamber partitioning plate 4 through flange plate 208 and a bolt. The pipeline body includes a front part located in the test soil chamber 8 and a rear part located in the soil filtration chamber 10. The pipeline body 201 is provided with crack 202. The crack 202 is provided adjacent to the transparent observation window, and a seepage path can only pass through the crack. Those skilled in this field can replace damaged pipeline models with different parameters such as size and stiffness according to actual needs.

The electric push rod assembly can be provided on the front end cover through a bolt. A top pipe of a push rod of the electric push rod assembly is covered with high-density rubber plug 207 to achieve an effect of squeezing and waterproofing. In this embodiment, a direction of the crack 202 is adjusted by changing a mounting angle of the simulated damaged pipeline body, and the size and shape of the crack 202 are adjusted by changing a squeezing force of the rubber plug 207 at an end of the electric push rod on the crack 202. For example, since the damaged pipeline model and the chamber partitioning plate are detachably connected, the pipeline body 201 is rotated a certain angle along a pipeline axis before it is mounted on the chamber partitioning plate 4. In this way, the direction of the crack 202 changes with the rotation of the pipeline body 201, thereby adjusting the direction of the crack 202 at the front end of the damaged pipeline model 2. The crack 202 at the front end of the damaged pipeline model 2 is resized by adjusting the squeezing force of the rubber plug 207 at the end of the electric push rod on the crack 202. In a complete squeezing situation, the crack 202 is completely blocked. As the squeezing force is gradually reduced, the rubber plug 207 gradually detaches from the crack 202, thereby adjusting the size and shape of the crack 202. The design can simulate different working conditions, so the test form can be modified without adjusting too many devices.

Figure 5:
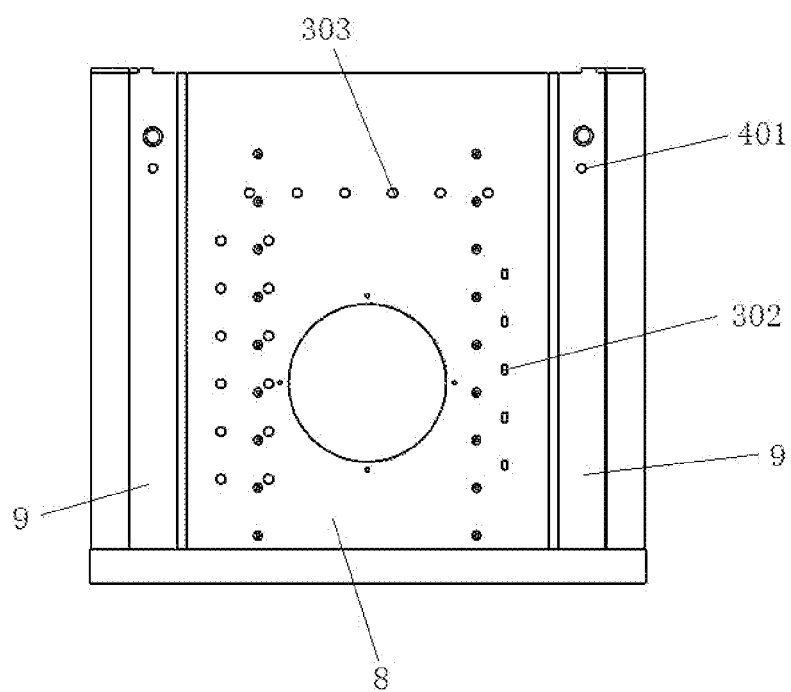
FIG. 5 is a front view of the testing device (with a front plate of the model box and a high-speed camera assembly removed) according to the embodiment of the present disclosure.

As shown in FIG. 5, the test soil chamber located in the middle and the seepage chambers located at the two sides of the test soil chamber are separated by the pair of permeable plates. The front end of the damaged pipeline model is located in the test soil chamber. During a test, a tested soil sample is filled into the test soil chamber, with a filling height determined based on the test. In this embodiment, the pair of permeable plates are symmetrically arranged and made of alloy steel porous permeable plates to avoid unnecessary scouring of the test soil chamber by water circulation. Meanwhile, the highest water level during the test is limited by the water level limiting hole that communicates the seepage chamber with the water circulation supply chamber. Soil pressure sensors 303 and pore pressure sensors 302 are arranged in a line array inside the soil. The soil pressure sensors 303 are configured to monitor a soil pressure of the test soil chamber during the testing process, while the pore pressure sensors 302 are configured to monitor the evolution of a pore pressure inside the test soil chamber in real time.

Figure 6:
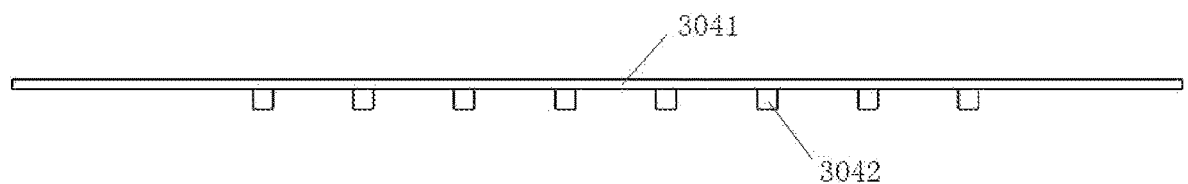
FIG. 6 is a schematic diagram of a laser displacement sensing device according to the embodiment of the present disclosure.

In a specific implementation of the present disclosure, laser displacement sensing device 304 for real-time measurement of soil surface displacement is further provided above the test soil chamber 8. As shown in FIG. 6, the laser displacement sensing device 304 includes laser displacement sensor connecting rod 3041 and laser displacement sensors 3042. The laser displacement sensors 3042 are provided in a line array on the laser displacement sensor connecting rod 3041. As shown in FIG. 2, the laser displacement sensor connecting rod 3041 is provided on upper parts of the right plate and the left plate of the model box through screw holes.

Figure 7A:
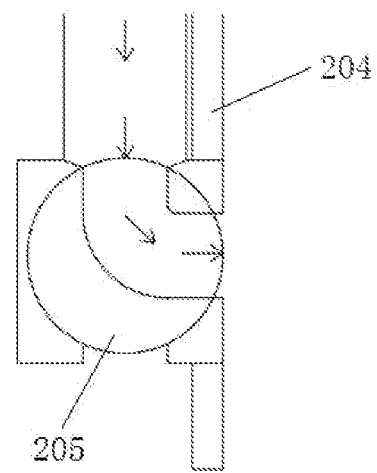
FIGS. 7A-7B are schematic diagrams of a ball valve device according to the embodiment of the present disclosure.
Figure 7B:
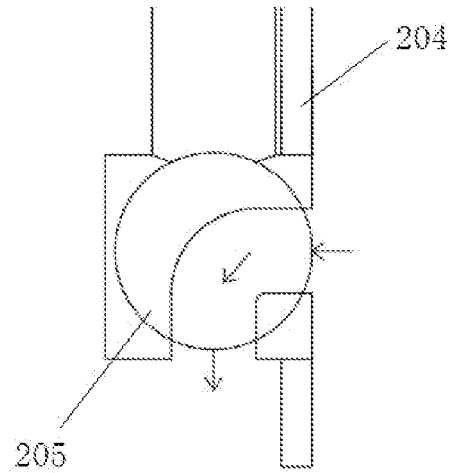

In a specific implementation of the present disclosure, as shown in FIGS. 7A-7B, the ball valve device 205 is rotatable to control the water supply and drainage conditions of the damaged pipeline, so as to control the water level inside the damaged pipeline model. The arrow in the figure shows the direction of water flow. FIG. 7A shows that the submersible pump supplies water to the pipeline, and FIG. 7B shows that the damaged pipeline drains freely.

Figure 8:
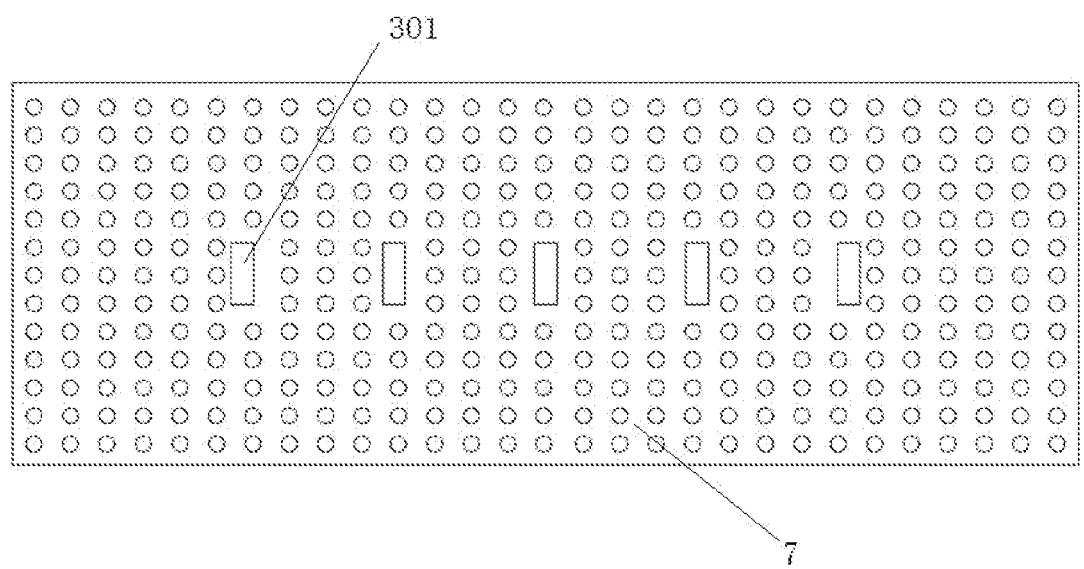
FIG. 8 is a schematic diagram of a filter plate and a strain detection assembly according to the embodiment of the present disclosure.

In a specific implementation of the present disclosure, the water-soil separation device in the soil filtration chamber 10 adopts multi-stage filtration, such that the water-soil mixture coming from the damaged pipeline is fully collected. Soil particles are used for post-test analysis, and the filtered water meets the working requirements of the submersible pump for water quality. As shown in FIG. 8, in this embodiment, the water-soil separation device is implemented by double-layer filter plates 7 with different leak radii. A pair of filter plates shown in FIG. 8 are directly inserted into reserved slots of the baffles located at the two sides. Strain monitoring assembly 301 is deployed on each layer of the filter plates for real-time monitoring of a strain of the filter plates. The water-soil mixture passes through the two filter plates with different leak radii in sequence. Soil particles with a particle size greater than a diameter of leak holes are blocked on the filter plate. Soil particles with different particle sizes are blocked on the two filter plates. The blocked soil particles cause a strain in the filter plate under the action of hypergravity. The strain monitoring assembly is previously provided on the filter plate for real-time monitoring of the strain of the filter plate. A stress is calculated through a mechanical method, and the escape behavior of soil particles is accurately described based on a real-time stress change.

Figure 9:
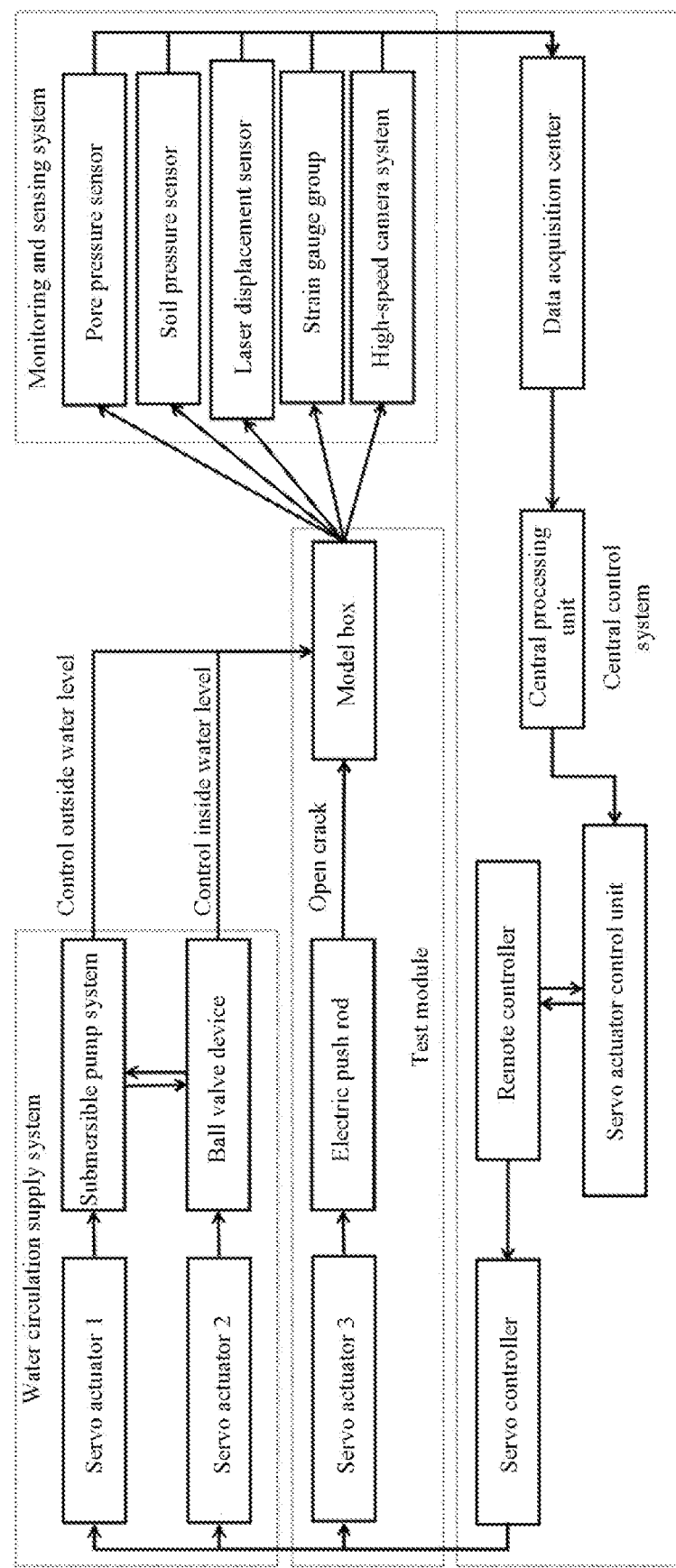
FIG. 9 is a schematic diagram of a working principle of the testing device according to the embodiment of the present disclosure.

As shown in FIG. 9, the strain monitoring assembly 301, the pore pressure sensors 302, the soil pressure sensors 303, the laser displacement sensing device 304, and the high-speed camera assembly 305 form the monitoring and sensing system. The laser displacement sensors are provided on the laser displacement sensor connecting rod for real-time monitoring of the surface deformation of the foundation soil. The pore pressure sensors 302 and the soil pressure sensors 303 are configured to monitor the real-time water level and soil pressure of the test soil chamber, thereby controlling a circulating water flow of the submersible pumps based on water level information. The strain monitoring assembly 301 provided on the water-soil separation device is configured to measure the strain of the water-soil separation device. The high-speed camera assembly 305 provided at the observation window 1011 on the front plate of the model box is configured for real-time photography of the testing process.

In a specific implementation of the present disclosure, a data collection center acquires data measured by the monitoring and sensing system, and resizes the crack and the internal and external water levels of the damaged pipeline model through a servo control system. In this embodiment, the servo control system includes a central processing unit, a servo actuator control unit, a remote controller, and a servo controller. The central processing unit acquires data from the data collection center, processes the data, and feeds back an action instruction. The instruction is transmitted from the servo actuator control unit to the local servo controller through the remote controller. The local device is provided with three servo actuators, which are respectively configured to adjust a circulating water volume and a flow direction of the water circulation supply chamber, switch the water inlet and outlet control device between water inlet and outlet functions, and resize the crack of the damaged pipeline model. For example, servo actuator 1 is configured to control the power of the submersible pump, allowing the submersible pump to complete water circulation at a certain speed so as to control the water level of the seepage chamber, thereby achieving real-time control of the water level outside the damaged pipeline model. Servo actuator 2 is configured to control the rotation of the ball valve to change the drainage condition of the damaged pipeline, and to control the submersible pump to supply water to the simulated damaged pipeline through the ball valve device so as to achieve testing simulation of full flow inside the pipeline. Servo actuator 3 is configured to control the squeezing force of the rubber plug at the end of the electric push rod on the crack so as to resize the crack.

In a specific implementation of the present disclosure, the working efficiency of the submersible pump meets the requirement of a desired water circulation speed under the gravitational acceleration (Ng). The observation window on the front plate of model box is made of organic glass with a transmittance of ≥85%, which can resist a lateral pressure of the soil under hypergravity and meet the requirement of clarity. The high-speed camera assembly meets the requirements of stable and clear shooting under hypergravity. The laser displacement sensor ensures monitoring accuracy under hypergravity, and the connecting rod avoids excessive deformation so as to avoid large system errors. In addition, a waterproof measure is taken between the model box and the internal structure. The waterproof measure is also taken at all bolt connection positions and plate joints. Specifically, the waterproof measure needs to ensure that the deformation and strength of the model box adapt to the gravitational acceleration (Ng) and the requirement for isolating each chamber.

In a specific implementation of the present disclosure, a process of simulating a ground subsidence induced by buried pipeline leakage and infiltration through the centrifugal model testing device includes the following steps.

Preparation stage: model soil is filled in the test soil chamber 8 of the centrifugal model testing device, and circulating water is injected into the water circulation supply chambers 11.

Simulation test stage: infiltration of water into the damaged pipeline model and leakage of water from the damaged pipeline model are alternately performed.

When the infiltration of water into the damaged pipeline model is performed, the water inlet and outlet control device of the damaged pipeline model 2 is switched to a water outlet condition to control the water circulation supply chambers 11 to supply water to the seepage chambers 9. The water level outside the damaged pipeline model is stably controlled by adjusting the height of the water level limiting hole 401 of the chamber partitioning plate. The water in the seepage chambers 9 seeps into the soil in the test soil chamber 8, and a water-soil mixture flows into the damaged pipeline model 2 from the crack 202 at the front end of the damaged pipeline model 2, and is discharged from the rear end of the damaged pipeline model 2. After being filtered by the water-soil separation device in the soil filtration chamber 10, the water enters the water circulation supply chambers 11 to achieve water circulation. In this simulation process, real-time monitoring of the soil pressure, water pressure and soil surface displacement of the test soil chamber 8 and the strain of the water-soil separation device in the soil filtration chamber 10 is carried out, and the real-time loss of soil particles is obtained based on the strain.

When the leakage of water from the damaged pipeline model is performed, the water inlet and outlet control device of the damaged pipeline model 2 is switched to a water inlet condition to control the water circulation supply chambers 11 to supply water to the damaged pipeline model 2. The water in the damaged pipeline model 2 flows into the soil in the test soil chamber 8 from the crack 202 at the front end, and seeps into the seepage chambers 9 located at the two sides of the test soil chamber 8. The water level outside the damaged pipeline model is stably controlled by adjusting the height of the water level limiting hole 401 of the chamber partitioning plate. When the water level outside the damaged pipeline model reaches the height of the water level limiting hole 401, the water in the seepage chambers 9 flows back into the water circulation supply chambers 11, achieving water circulation. During this simulation process, real-time monitoring of the soil pressure, water pressure, and soil surface displacement of the test soil chamber 8 is carried out.

In a specific implementation of the present disclosure, in the preparation stage, the direction of the crack 202 at the front end of the damaged pipeline model 2 is adjusted by changing the connection angle between the damaged pipeline model 2 and the chamber partitioning plate 4. In the simulation test stage, the crack 202 at the front end of the damaged pipeline model 2 is resized by adjusting the squeezing force of the rubber plug 207 at the end of the electric push rod on the crack 202. The specific process is as follows.

When a normal service condition is simulated, the electric push rod is controlled to drive the rubber plug 207 at the end to extend, allowing the rubber plug 207 to tightly contact with the crack 202, such that the crack 202 is completely blocked.

When a damaged crack condition is simulated, the electric push rod is controlled to drive the rubber plug 207 at the end to retract, and a degree of detachment between the rubber plug 207 and the crack 202 is controlled by adjusting an amount of retraction, thereby resizing the crack 202.

The above described are merely preferred implementations of the present disclosure and is not intended to limit the present disclosure, and various changes and modifications of the present disclosure may be made by those skilled in the art. Any modification, equivalent substitution, improvement, etc. within the spirit and principles of the present disclosure shall fall within the scope of protection of the present disclosure.

What is claimed is:

1. A centrifugal testing device for simulating ground subsidence induced by buried pipeline leakage and infiltration, comprising a model box, a damaged pipeline model, a servo control system, and a monitoring and sensing system, wherein the model box is internally divided into a front part and a rear part by a chamber partitioning plate; and the chamber partitioning plate is provided with a mounting hole for fixing the damaged pipeline model;

the front part of the model box is provided with a test soil chamber and seepage chambers located at two sides of the test soil chamber; a front end of the damaged pipeline model in the test soil chamber is provided with a crack having an adjustable size; the rear part of the model box is provided with a soil filtration chamber and water circulation supply chambers located at two sides of the soil filtration chamber; a rear end of the damaged pipeline model in the soil filtration chamber is provided with a water inlet and outlet control device; a water-soil separation device is provided below the water inlet and outlet control device; and the chamber partitioning plate is provided with a water level limiting hole for communicating the seepage chamber with the water circulation supply chamber;

the servo control system is configured to resize the crack of the damaged pipeline model and control water levels inside and outside the damaged pipeline model; and the monitoring and sensing system is configured to measure a soil pressure, a water pressure and a soil surface displacement of the test soil chamber and a strain of the water-soil separation device in the soil filtration chamber in real time;

the damaged pipeline model comprises a pipeline body, a front end cover, a rear end cover, and an electric push rod assembly; wherein the pipeline body is fixed into the mounting hole of the chamber partitioning plate through a flange plate; the front end cover and the rear end cover are configured to seal front and rear ends of the pipeline body, respectively; the crack is located at a position of the pipeline body adjacent to the front end cover; the electric push rod assembly is provided at an inner side of the front end cover; and a rubber plug at an end of an electric push rod is configured to resize the crack; and the soil filtration chamber is separated from the water circulation supply chambers at the two sides of the soil filtration chamber by a pair of baffles; a bottom part of the baffle is provided with a hole for communicating the soil filtration chamber with the water circulation supply chamber; and the water-soil separation device is fixed inside the soil filtration chamber by the baffles and located below the damaged pipeline model.

2. The centrifugal testing device for simulating ground subsidence induced by buried pipeline leakage and infiltration according to claim 1, wherein the water inlet and outlet control device is provided with a ball valve device; and the ball valve device is provided on the rear end cover to switch the damaged pipeline model between water inlet and outlet conditions.

3. The centrifugal testing device for simulating ground subsidence induced by buried pipeline leakage and infiltration according to claim 1, wherein the water-soil separation device is a single-layer or multi-layer filter plate.

4. The centrifugal testing device for simulating ground subsidence induced by buried pipeline leakage and infiltration according to claim 1, wherein a submersible pump is provided in the water circulation supply chamber; and the submersible pump is connected to the water inlet and outlet control device of the damaged pipeline model and the seepage chamber through a controllable water outlet pipe.

5. The centrifugal testing device for simulating ground subsidence induced by buried pipeline leakage and infiltration according to claim 1, wherein the monitoring and sensing system comprises a strain monitoring assembly, pore pressure sensors, soil pressure sensors, a laser displacement sensing device, and a high-speed camera assembly; and the pore pressure sensors and the soil pressure sensors are arranged in a line array in different layers in soil inside the test soil chamber; the laser displacement sensing device is provided in a line array above the test soil chamber to measure a soil surface displacement inside the test soil chamber; the strain monitoring assembly is provided on the water-soil separation device to measure the strain of the water-soil separation device; and the high-speed camera assembly is provided at an observation window at a front plate of the model box.

6. The centrifugal testing device for simulating ground subsidence induced by buried pipeline leakage and infiltration according to claim 1, wherein the servo control system comprises a servo controller and a plurality of servo actuators; and each of the servo actuators is configured to adjust a circulating water volume and a flow direction of the water circulation supply chambers, switch the water inlet and outlet control device between water inlet and outlet functions, and resize the crack of the damaged pipeline model.

7. A testing method of the centrifugal testing device for simulating ground subsidence induced by buried pipeline leakage and infiltration according to claim 1, comprising:

preparation stage: filling model soil in the test soil chamber of the centrifugal model testing device, and injecting circulating water into the water circulation supply chambers; and simulation test stage: alternately performing infiltration of water into the damaged pipeline model and leakage of water from the damaged pipeline model:

simulating the infiltration of water into the damaged pipeline model: switching the water inlet and outlet control device of the damaged pipeline model to a water outlet condition, and controlling the water circulation supply chambers to supply water to the seepage chambers; stably controlling a water level outside the damaged pipeline model by adjusting a height of the water level limiting hole of the chamber partitioning plate; allowing the water in the seepage chambers to seep into the soil in the test soil chamber; allowing a water-soil mixture to flow into the damaged pipeline model from the crack at the front end of the damaged pipeline model and to leave from the rear end of the damaged pipeline model; allowing water filtered by the water-soil separation device in the soil filtration chamber to enter the water circulation supply chambers, thereby achieving water circulation; monitoring, in the simulation process, the soil pressure, the water pressure and the soil surface displacement of the test soil chamber and the strain of the water-soil separation device in the soil filtration chamber in real time, and obtaining a real-time loss of soil particles based on the strain; and simulating the leakage of water from the damaged pipeline model: switching the water inlet and outlet control device of the damaged pipeline model to a water inlet condition, and controlling the water circulation supply chambers to supply water to the damaged pipeline model; allowing the water in the damaged pipeline model to flow into the soil in the test soil chamber from the crack at the front end and to seep into the seepage chambers at the two sides of the test soil chamber; stably controlling the water level outside the damaged pipeline model by adjusting the height of the water level limiting hole of the chamber partitioning plate; allowing, when the water level outside the damaged pipeline model reaches the height of the water level limiting hole, the water in the seepage chambers to flow back into the water circulation supply chambers, thereby achieving water circulation; and monitoring, in the simulation process, the soil pressure, the water pressure and the soil surface displacement of the test soil chamber in real time.

8. The testing method of the centrifugal testing device for simulating ground subsidence induced by buried pipeline leakage and infiltration according to claim 7, wherein in the preparation stage, a direction of the crack at the front end of the damaged pipeline model is adjusted by changing a connection angle between the damaged pipeline model and the chamber partitioning plate; and in the simulation test stage, the crack at the front end of the damaged pipeline model is resized by adjusting a squeezing force of the rubber plug at the end of the electric push rod on the crack:

when a normal service condition is simulated, the electric push rod is controlled to drive the rubber plug at the end to extend, allowing the rubber plug to tightly contact with the crack, such that the crack is completely blocked; and when a damaged crack condition is simulated, the electric push rod is controlled to drive the rubber plug at the end to retract, and a degree of detachment between the rubber plug and the crack is controlled by adjusting an amount of retraction, thereby resizing the crack.

9. The testing method of the centrifugal testing device for simulating ground subsidence induced by buried pipeline leakage and infiltration according to claim 7, wherein the water inlet and outlet control device is provided with a ball valve device; and the ball valve device is provided on the rear end cover to switch the damaged pipeline model between the water inlet and outlet conditions.

10. The testing method of the centrifugal testing device for simulating ground subsidence induced by buried pipeline leakage and infiltration according to claim 7, wherein the water-soil separation device is a single-layer or multi-layer filter plate.

11. The testing method of the centrifugal testing device for simulating ground subsidence induced by buried pipeline leakage and infiltration according to claim 7, wherein a submersible pump is provided in the water circulation supply chamber; and the submersible pump is connected to the water inlet and outlet control device of the damaged pipeline model and the seepage chamber through a controllable water outlet pipe.

12. The testing method of the centrifugal testing device for simulating ground subsidence induced by buried pipeline leakage and infiltration according to claim 7, wherein the monitoring and sensing system comprises a strain monitoring assembly, pore pressure sensors, soil pressure sensors, a laser displacement sensing device, and a high-speed camera assembly; and the pore pressure sensors and the soil pressure sensors are arranged in a line array in different layers in soil inside the test soil chamber; the laser displacement sensing device is provided in a line array above the test soil chamber to measure a soil surface displacement inside the test soil chamber; the strain monitoring assembly is provided on the water-soil separation device to measure the strain of the water-soil separation device; and the high-speed camera assembly is provided at an observation window at a front plate of the model box.

13. The testing method of the centrifugal testing device for simulating ground subsidence induced by buried pipeline leakage and infiltration according to claim 7, wherein the servo control system comprises a servo controller and a plurality of servo actuators; and each of the servo actuators is configured to adjust a circulating water volume and a flow direction of the water circulation supply chambers, switch the water inlet and outlet control device between water inlet and outlet functions, and resize the crack of the damaged pipeline model.

\* \* \* \* \*